(12) United States Patent
Sklar et al.

(10) Patent No.: US 9,924,996 B2
(45) Date of Patent: *Mar. 27, 2018

(54) ANCHORED CARDIAC ABLATION CATHETER

(71) Applicant: Ablacor Medical Corporation, Needham, MA (US)

(72) Inventors: Martin J. Sklar, Needham, MA (US); Howard E. Guthermann, Newton, MA (US); Howard Ring, Newton, MA (US)

(73) Assignee: Ablacor Medical Corporation, Needham, MA (US)

( * ) Notice: Subject to any disclaimer, the term of this patent is extended or adjusted under 35 U.S.C. 154(b) by 159 days.

This patent is subject to a terminal disclaimer.

(21) Appl. No.: 13/666,615

(22) Filed: Nov. 1, 2012

(65) Prior Publication Data

US 2013/0060248 A1 Mar. 7, 2013

Related U.S. Application Data

(63) Continuation of application No. 13/101,270, filed on May 5, 2011.
(Continued)

(51) Int. Cl.
*A61B 18/14* (2006.01)
*A61F 5/01* (2006.01)
(Continued)

(52) U.S. Cl.
CPC .......... *A61B 18/14* (2013.01); *A61B 18/1492* (2013.01); *A61F 5/0127* (2013.01);
(Continued)

(58) Field of Classification Search
CPC ........... A61B 2018/00273; A61B 2018/00375; A61B 2018/1435; A61B 2018/1437
See application file for complete search history.

(56) References Cited

U.S. PATENT DOCUMENTS 5,125,928 A 6/1992 Parins et al.
5,562,722 A 10/1996 Racz et al.
(Continued)

FOREIGN PATENT DOCUMENTS

WO 2005046461 A1 5/2005

OTHER PUBLICATIONS

"Couple." Merriam-Webster.com. Merriam-Webster, n.d. Web. Feb. 3, 2016.*
(Continued)

*Primary Examiner* — Jaymi Della
*Assistant Examiner* — Eunhwa Kim
(74) *Attorney, Agent, or Firm* — Brown Rudnick LLP; Adam M. Schoen

(57) ABSTRACT

An apparatus and method for performing cardiac ablations employs a catheter comprising an anchoring device and an ablating device to perform the ablations to electrically isolate the pulmonary veins and left atrium from surrounding atrial tissue. The anchor can comprise a balloon-type device, a stent-like device, a strut-like device, a spring-strut-like device, an umbrella-like device, a mushroom-like device, or other device that allows the catheter to maintain a position with respect to target tissue. The ablator can comprise a balloon ablator, an umbrella ablator, a pinwheel ablator, an umbrella ablator incorporating a cinch mechanism, a mushroom balloon ablator and a segmented balloon or pinwheel ablator. The anchor and ablator can also comprise a combination mushroom balloon anchor section and mushroom balloon ablator section. The anchor and ablator can include electrodes for measuring a conductance therebetween when in deployed position, so as to determine the effectiveness of the ablation.

12 Claims, 13 Drawing Sheets

Related U.S. Application Data

(60) Provisional application No. 61/331,537, filed on May 5, 2010.

(51) Int. Cl.
  *A61B 18/00* (2006.01)
  *A61B 34/20* (2016.01)
  *A61B 90/00* (2016.01)

(52) U.S. Cl.
  CPC ............ *A61B 2018/0016* (2013.01); *A61B 2018/00261* (2013.01); *A61B 2018/00285* (2013.01); *A61B 2018/00357* (2013.01); *A61B 2018/00577* (2013.01); *A61B 2018/00839* (2013.01); *A61B 2018/00875* (2013.01); *A61B 2034/2063* (2016.02); *A61B 2090/065* (2016.02)

(56) References Cited

U.S. PATENT DOCUMENTS

| | | | |
|---|---|---|---|
| 5,876,399 | A | 3/1999 | Chia et al. |
| 5,906,591 | A | 5/1999 | Dario et al. |
| 5,971,983 | A | 10/1999 | Lesh |
| 6,063,081 | A | 5/2000 | Mulier et al. |
| 6,200,311 | B1 | 3/2001 | Danek et al. |
| 6,254,599 | B1 | 7/2001 | Lesh et al. |
| 6,305,378 | B1 | 10/2001 | Lesh |
| 6,416,511 | B1 | 7/2002 | Lesh et al. |
| 6,463,332 | B1 | 10/2002 | Aldrich |
| 6,471,697 | B1 | 10/2002 | Lesh |
| 6,517,477 | B1 | 2/2003 | Wendlandt |
| 6,527,769 | B2 | 3/2003 | Langberg et al. |
| 6,529,756 | B1 | 3/2003 | Phan et al. |
| 6,595,989 | B1 | 7/2003 | Schaer |
| 6,652,517 | B1 | 11/2003 | Hall et al. |
| 6,752,805 | B2 | 6/2004 | Maguire et al. |
| 6,764,486 | B2 | 7/2004 | Natale |
| 6,770,070 | B1 * | 8/2004 | Balbierz ............... 606/41 |
| 6,771,533 | B2 | 8/2004 | Witcraft et al. |
| 6,855,144 | B2 | 2/2005 | Lesh |
| 6,872,205 | B2 | 3/2005 | Lesh et al. |
| 6,893,438 | B2 | 5/2005 | Hall et al. |
| 6,893,442 | B2 | 5/2005 | Whayne |
| 6,955,173 | B2 | 10/2005 | Lesh |
| 6,964,660 | B2 | 11/2005 | Maguire et al. |
| 6,979,331 | B2 | 12/2005 | Hintringer et al. |
| 7,008,418 | B2 | 3/2006 | Hall et al. |
| 7,063,698 | B2 | 6/2006 | Whayne et al. |
| 7,066,880 | B2 | 6/2006 | Wendlandt |
| 7,156,816 | B2 | 1/2007 | Schwartz et al. |
| 7,655,005 | B2 | 2/2010 | Bhola |
| 7,753,906 | B2 | 7/2010 | Esposito |
| 2002/0065515 | A1 * | 5/2002 | Falwell ............ A61B 18/1492 606/41 |
| 2002/0107478 | A1 | 8/2002 | Wendlandt |
| 2002/0156499 | A1 | 10/2002 | Konya et al. |
| 2002/0173774 | A1 | 11/2002 | Olsen |
| 2003/0060821 | A1 | 3/2003 | Hall et al. |
| 2003/0065250 | A1 | 4/2003 | Chiel et al. |
| 2003/0069578 | A1 | 4/2003 | Hall et al. |
| 2003/0069587 | A1 | 4/2003 | Schorgl et al. |
| 2003/0078574 | A1 * | 4/2003 | Hall .................. A61B 18/1492 606/41 |
| 2003/0093072 | A1 * | 5/2003 | Friedman ............... 606/41 |
| 2003/0120270 | A1 | 6/2003 | Acker |
| 2003/0167056 | A1 | 9/2003 | Jahns et al. |
| 2004/0034347 | A1 | 2/2004 | Hall et al. |
| 2004/0236320 | A1 | 11/2004 | Protsenko et al. |
| 2004/0267337 | A1 | 12/2004 | Hayzelden |
| 2005/0154376 | A1 | 7/2005 | Riviere et al. |
| 2005/0182392 | A1 | 8/2005 | Brucker et al. |
| 2005/0222557 | A1 | 10/2005 | Baxter et al. |
| 2005/0235996 | A1 | 10/2005 | Hooser et al. |
| 2005/0240116 | A1 | 10/2005 | Saadat et al. |
| 2005/0273095 | A1 * | 12/2005 | Taimisto ............ A61B 18/1492 606/41 |
| 2006/0025756 | A1 | 2/2006 | Francischelli et al. |
| 2006/0084960 | A1 | 4/2006 | Mester et al. |
| 2006/0089635 | A1 | 4/2006 | Young et al. |
| 2006/0106298 | A1 | 5/2006 | Ahmed et al. |
| 2006/0106375 | A1 * | 5/2006 | Werneth ............ A61B 18/1492 606/32 |
| 2006/0200124 | A1 | 9/2006 | Whayne et al. |
| 2006/0206113 | A1 | 9/2006 | Whayne et al. |
| 2006/0235381 | A1 | 10/2006 | Whayne et al. |
| 2006/0247607 | A1 * | 11/2006 | Cornelius .......... A61B 18/1492 606/1 |
| 2007/0083193 | A1 | 4/2007 | Werneth et al. |
| 2007/0083194 | A1 * | 4/2007 | Kunis ................ A61B 18/1815 606/41 |
| 2007/0249999 | A1 | 10/2007 | Sklar et al. |
| 2007/0265609 | A1 | 11/2007 | Thapliyal et al. |
| 2007/0265610 | A1 | 11/2007 | Thapliyal et al. |
| 2008/0027423 | A1 | 1/2008 | Choi et al. |
| 2008/0249518 | A1 | 10/2008 | Warnking et al. |
| 2008/0281322 | A1 | 11/2008 | Sherman et al. |
| 2008/0294158 | A1 | 11/2008 | Pappone et al. |
| 2009/0221996 | A1 | 9/2009 | Lesh |
| 2009/0312755 | A1 | 12/2009 | Thapliyal et al. |
| 2010/0049099 | A1 | 2/2010 | Thapliyal et al. |
| 2015/0342675 | A1 | 12/2015 | Highsmith |

OTHER PUBLICATIONS

Supplementary European Search Report for Application No. 11778338.1, dated Oct. 22, 2013, 5 pages.
Patronik, et al., "A Miniature Cable-Driven Robot for Crawling on the Heart," Engineering in Medicine and Biology, May 2, 2005, pp. 5771-5774, Publisher: National Science Foundation, Published in Shanghai, China.
Patronik, et al., "Crawling on the Heart: A Mobile Robotic Device for Minimally Invasive Cardiac Interventions," Sep. 1, 2004, Publisher: Springer-Verlag 2004, Published in Pittsburgh, PA.
Patronik, et al., "Development of a Tethered Epicardial Crawler for Minimally Invasive Cardiac Therapies," Apr. 1, 2004, pp. 239-240, Publisher: IEEE, Published in Pittsburg, PA.
Razjouyan, et al., "Enhancing the Locomotion of an In Vivo Robot for Cardiac Surgery," Apr. 1, 2006, pp. 97-98, Published in Pittsburg, PA.
Riviere, et al., "Prototype Epicardial Crawling Device for Intrapericardial Intervention on the Beating Heart," The Heart Surgery Forum, Sep. 16, 2004, pp. E639-E643, vol. 7, No. 6, Publisher: Forum Multimedia Publishing, LLC, Published in Pittsburgh, PA.
International Preliminary report on Patentability for Application PCTUS2011035348 dated Nov. 15, 2012.

* cited by examiner

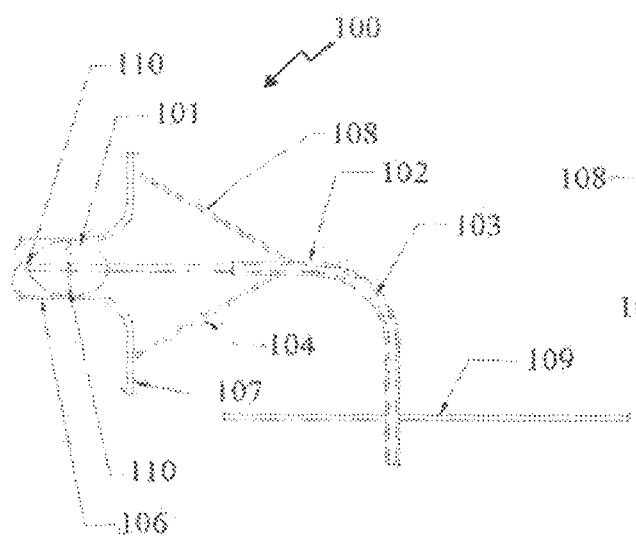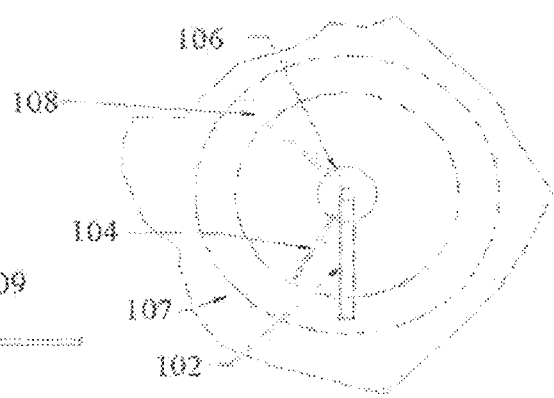
Fig. 1A  Fig. 1B
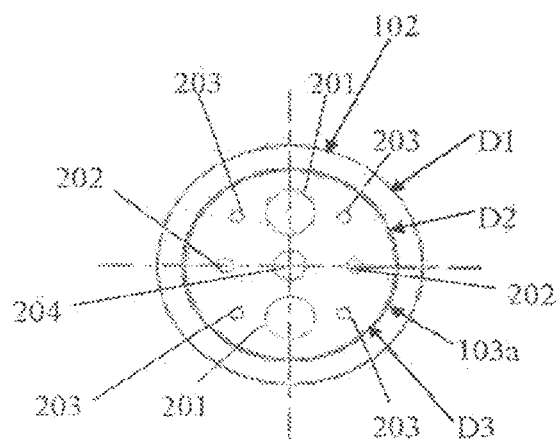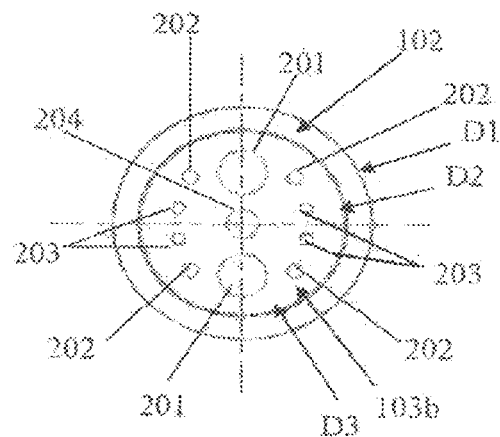
Fig. 2A  Fig. 2B

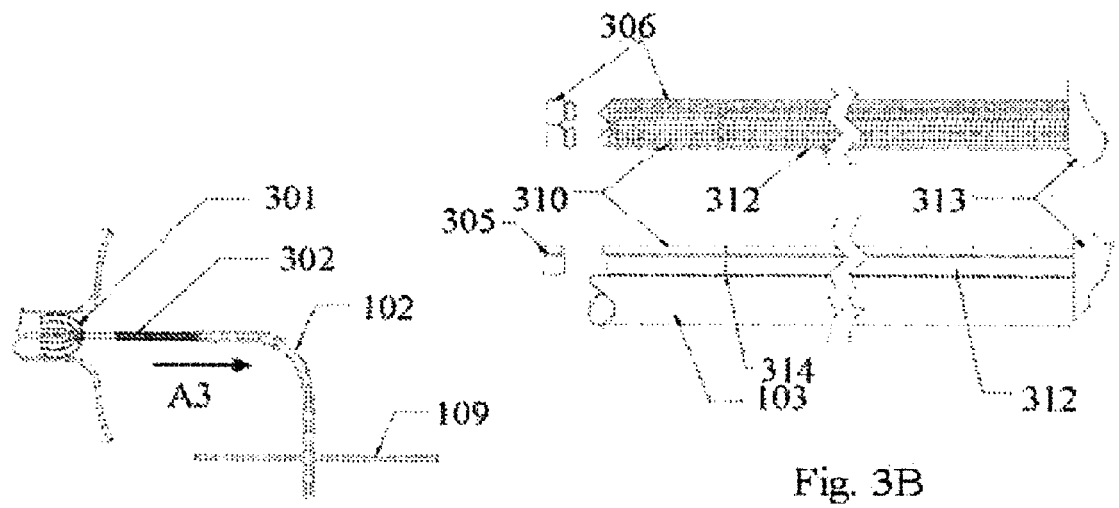
Fig. 3A
Fig. 3B
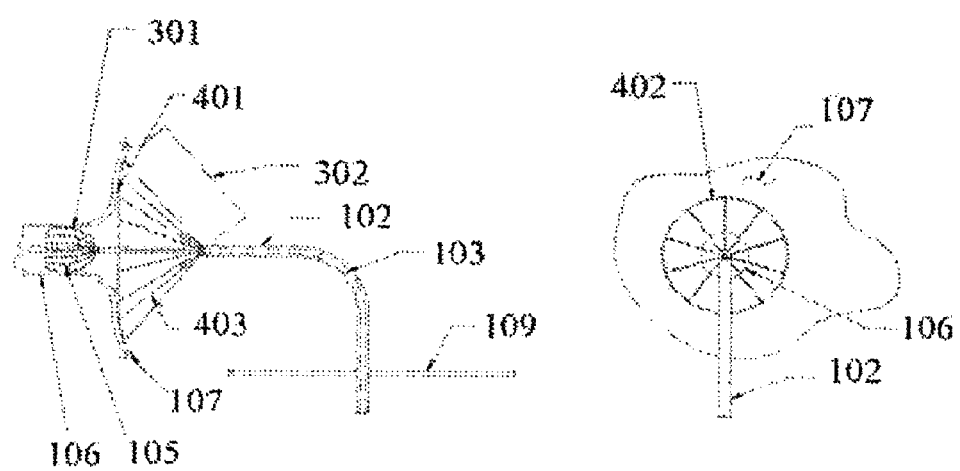
Fig. 4A
Fig. 4B

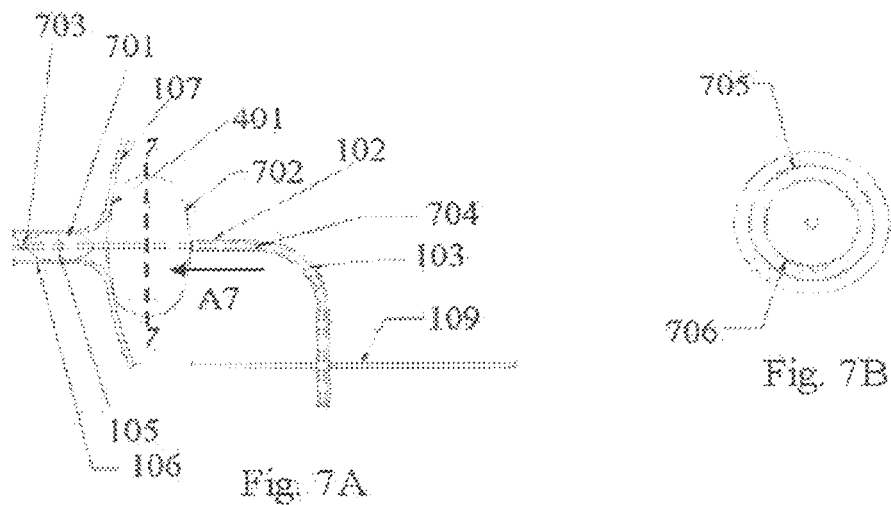
Fig. 7A
Fig. 7B
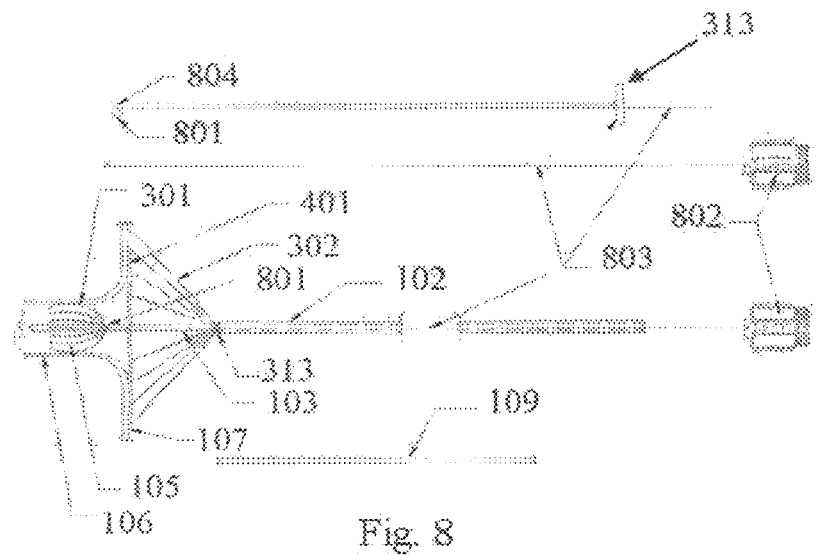
Fig. 8

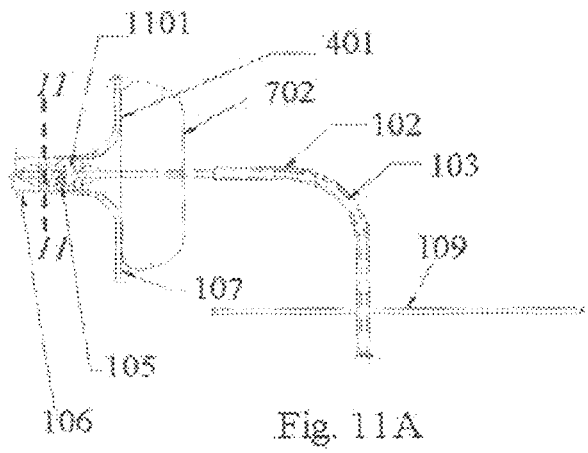
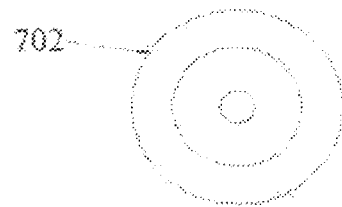
Fig. 11C
Fig. 11B
Fig. 11A
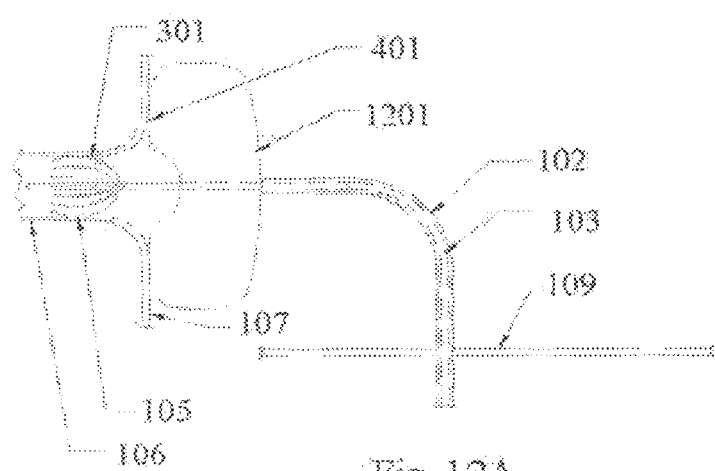
Fig. 12A
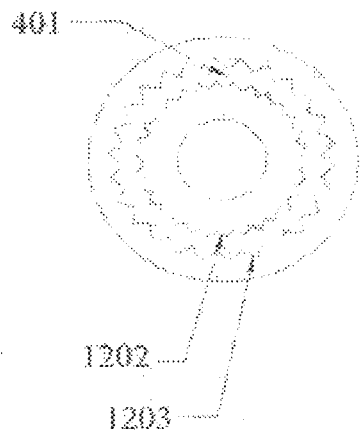
Fig. 12B

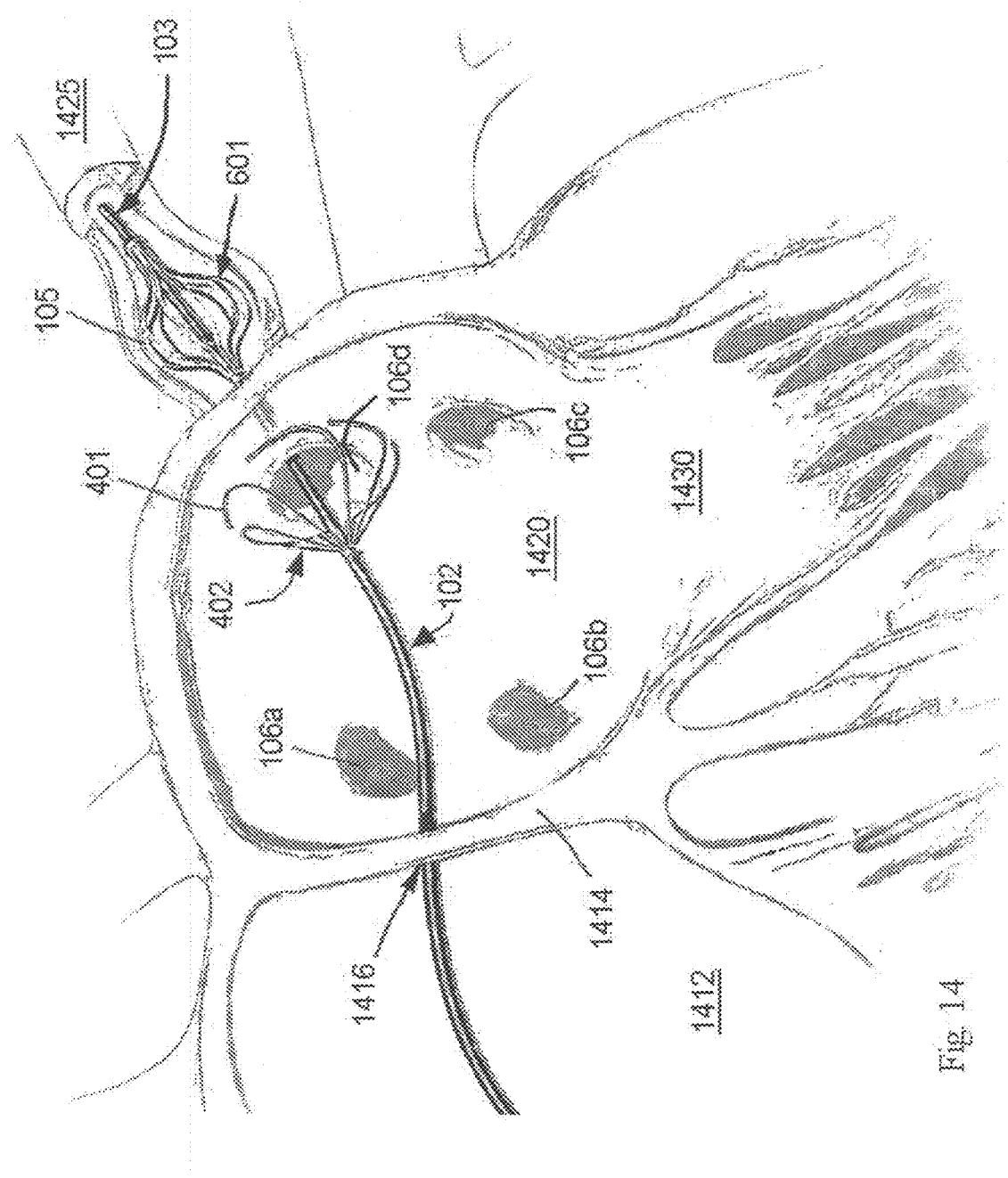

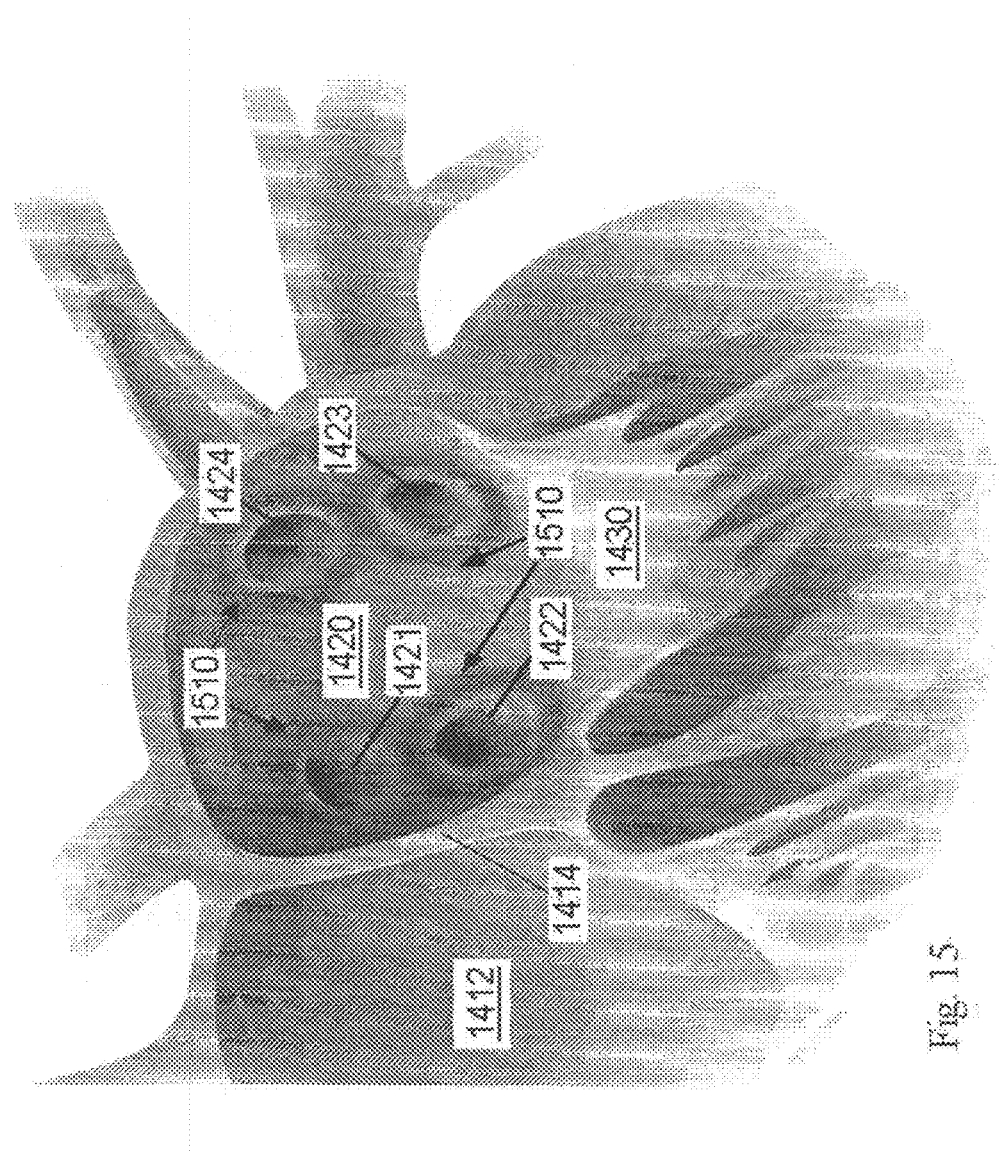

ANCHORED CARDIAC ABLATION CATHETER

RELATED APPLICATIONS

This application is a continuation application of U.S. nonprovisional application Ser. No. 13/101,270, filed May 5, 2011, which claims the benefit of U.S. Provisional Patent Application Ser. No. 61/331,537, filed May 5, 2010, entitled ANCHORED RING CARDIAC ABLATION CATHETER, the entire disclosure of each of which is herein incorporated by reference.

FIELD OF THE INVENTION

This invention relates to cardiac ablation devices and methods for using the same.

BACKGROUND OF THE INVENTION

Atrial fibrillation (AF) is an arrhythmic condition of the heart in which the normal cardiac electrical impulses spread through the atrium in an incoherent manner, preventing the atrium from efficiently delivering blood to the ventricle. It is estimated that over 2.2 million Americans and 4.5 million EU citizens suffer from atrial fibrillation. Annual costs in the U.S. related to AF are approximately $16 billion. There are approximately 300,000 new AF cases each year. Contributors to AF incidence include the aging population, and many conditions including hypertension, cardiomyopathy, structural heart disease, diabetes, sleep apnea and obesity. Approximately 15% of stroke cases are due to clots originating in blood pooling in the atria due to AF. AF is classified into several types, primarily paroxysmal, and chronic, which includes persistent, and permanent with subtypes, depending on the presentation and associated morbidities. First-line treatment of AF is pharmaceutical, either through rate control, rhythm control, anticoagulation, or some combination. Due to the multiple types of AF, and the many agents and protocols used, the overall success of drug treatment cannot be accurately stated; some estimates are that overall drug efficacy is <40%. Additionally, some drug treatments have side effects that reduce quality of life or present risks.

When drug treatment is unsatisfactory, AF can be treated by destruction of the paths through which the erratic electrical impulses are spread. The destruction can be accomplished from either the epicardial or the endocardial surface, and by either mechanical means, such as the Cox Maze surgery in which tissue dissection disrupts those unwanted electrical pathways, or by application of energy to the tissue. Energetic ablation can be performed using radio frequency (RF) energy, microwave energy, ultrasonics, or cryotherapy, among others. The goal of ablation is to create a continuous, fully transmural line of necrosed tissue, which are able to conduct electrical signals across the line, effectively creating an electrical fence. However, today's ablation techniques are complex and have not reached high efficacy, thereby limiting their clinical utility. A particular problem is that clinicians cannot easily determine during the procedure whether the ablation produced is likely to interrupt conduction permanently.

About 20% of ablations are epicardial; this route is chosen when other treatments have failed, and when cardiac surgical procedures are also needed, as epicardial ablation generally requires heart bypass. The remaining 80% are endocardial, performed using a percutaneous catheter inserted into a vein, then into the right atrium, and then via a trans-septal puncture through the septum into the left atrium. The most common ablation techniques attempt to create circumferential ablations around the ostia, the locations where the pulmonary veins (PV) enter the left atrium. This isolates the disorganized signals arising in the veins from the atrium, without inducing stenosis due to pulmonary vein ablations. However, of the approximately 1 million AF patients in the US not successfully treated with drugs, only about 100,000 are treated by ablation annually. More are not treated by ablation due to its difficulty and the wide variation in treatment efficacy. Approximately 40% are repeat ablation procedures.

Endocardial catheter ablation is currently a two to six hour procedure performed by electrophysiologists (EPs). Much of this time is needed for a spot by spot creation of the required circumferential ablations using the ablation tools currently available, along with the time spent to verify conduction block, and follow-up during the procedure to insure that conduction block has been maintained, and when not, reablate specific locations as determined via conduction measurements. Reported long term success rates range from 20-70%. The efficacy decreases as AF progresses. To achieve even these results, approximately 40% of patients require repeat procedures at significant cost to the healthcare system, along with the radiation exposure from imaging and other risks to the patient and to the clinician inherent in these procedures. Market research indicates that both the variations in efficacy and the lengthy duration of the procedure are primarily due to uncertainty on the part of the clinician during the procedure as to whether the ablation lesion is continuous, complete, permanent, and transmural.

Present commercial minimally invasive catheter ablators consist of numerous single point ablation catheters, as well as a number of more recent devices, including a balloon catheter utilizing a laser energy source, a balloon catheter utilizing cryothermal energy, a multi-electrode ablator, utilizing RF energy and various robotic systems to maneuver catheters through the vascular system into the heart.

The two balloon ablators are applied in a similar manner, as they are inserted via a catheter and placed at the ostium, or intersection of the pulmonary veins with the atrial wall. Their placement limits their application to only electrically isolating unwanted signals around the pulmonary veins from the rest of the heart. Electrophysiologists, who perform the ablation procedures have also indicated that follow-up spots still need to be ablated, and there have been reports of injuries to surrounding tissue such as the phrenic and vagus nerves, and stenosis of the veins. Since they occlude blood flow through the vein, the balloons need to be adequately stiff to oppose the pressure from the blood flow. This is desirable in order to maintain their position and contact with the target tissue during the ablation cycle, otherwise they are less likely to achieve a continuous abaltion.

The multi-electrode array ablator, mounted on a Nitinol frame, can be used to map, ablate, and verify the ablation line by measuring conduction block, across the ablation line, around the pulmonary veins or in other target areas. Although this device can use its Nitinol frame to more readily conform to the target surface, while using a low level of applied force, which can provide enhanced contact to maximize ablation energy transfer, electrophysiologists have reported that this requires additional discrete point ablations to be performed. This increases procedure time and reduces the likelihood of generating a continuous, fully transmural ablation. To maintain contact between the array and target tissue requires the electrophysiologist to continue to apply force during the ablation cycle, similar to point and balloon ablators. Because each ablator electrode in the array resides in a continuous ring, it may not satisfactorily conform to the target tissue's topography.

There are a number of robotic systems in development and already commercialized that augment the clinician's ability to maneuver the catheter to the selected target in the vascular system, including chambers in the heart. One such robot system allows a magnet to direct a catheter to a target and hold it against the target. It is designed to maneuver and hold point ablators. Point ablators take significant procedure time and do not necessarily generate continuous lesion lines to block unwanted electrical pathways. In addition the robots are very expensive.

However, present methods and technology do not provide features for locating and fixing in place the ablative element(s) that are physically separate from the mechanism for performing the ablation. This lack of separation limits the capability of devices based on these prior inventions to accurately locate the tissue volume to be ablated with respect to the pulmonary vein target at a location which minimizes the possibility of pulmonary stenosis, while also adjusting the contact of the ablative element(s) to provide intimate and accurate contact of the ablative element(s) with the atrial tissue and thereby form an ablated volume that fully encloses the ostium of the pulmonary vein.

In addition, the balloons and multi-electrode array are constructed and arranged to apply a continuous ablation line. These technologies are limited because they must be in continuous contact throughout the ablator-tissue contact range. They have problems maintaining that contact during the ablation cycle.

Also, prior systems employ primarily only point ablators to generate lesion lines beyond the pulmonary vein isolation technique, which creates a circumferential abvlation around the pulmonary veins. However, this is a difficult procedure, which requires a high level of skill, exposes the clinicians and patient to radiation during imaging, extends procedure durations and reduces efficacy.

SUMMARY OF THE INVENTION

The present invention overcomes the disadvantages of the prior art by providing an apparatus and method for use in performing endocardial ablations to electrically isolate the pulmonary vein(s) from the surrounding atrial tissue. An illustrative embodiment of the apparatus is in the form of a catheter with an external sheath, retractable to various positions as known to those skilled in the art. In addition, a second embodiment provides the capability to perform linear ablation lines as well. According to various embodiments herein, the catheter is introduced into the pulmonary vein with a Guide catheter. An option is to provide steering within the main catheter, and to operate free of a guide catheter.

The catheter, at its distal end, is assembled with an anchoring device beneath the sheath so that the anchor expands upon initial refraction of the internal sheath. When the catheter tip has been placed within a pulmonary vein, and the sheath initially retracted, the anchoring device expands and contacts the interior wall of the pulmonary vein, and exerts a radial force on the wall, anchoring and centering the catheter with respect to the lumen of the pulmonary vein at that location. By also pulling the anchoring device in a proximal direction, (towards the user), the anchor will be too large to pull through the vein's exit into the atrium, thereby enhancing the anchoring device. Several specific embodiments of the anchoring device are presented below.

The catheter also includes, at a separate location proximal to that of the anchoring device, an ablation device. After the catheter has been anchored in the vein, an additional retraction of the external sheath allows the expansion of the ablation device. A variety of ablation device designs and implementations can be employed in according with various embodiments herein.

After deployment of the ablation device, a secondary manipulation of the catheter can be employed to force the ablation device components into intimate contact with the atrial tissue, prior to the initiation of the ablation step. Examples of actuators to carry out this illustrative secondary manipulation of the catheter are detailed in the drawings and specifications below.

Both the anchoring device and the ablation device can also employ additional electrical conductors, operatively connected to that catheter control system, and typically provided separate from the ablation control or the anchoring device. The additional conductors are placed in contact with the tissue generally remote from (away from) the ablated tissue volume, by the expansion of the anchoring and ablation devices, respectively. The additional conductors can be used, while the anchoring and ablation devices remain in place, to assess the presence or absence of conduction block across the volume of tissue ablated during or after the ablation process. This step prevents having to estimate where to place the feedback sensors with respect to the ablation volume. The use of such conductors to assess the presence or absence of conduction block through the ablated tissue volume is well known to those skilled in the art.

In order to optimize radio-frequency ablation, a bipolar circuit is typically desirable, so as to direct and focus the ablation energy in an efficient and safe manner. There are a number of options to create a bipolar conduction path. A typical method includes a conductive pad placed under the patient, but according to this method the energy will be disbursed in many directions. One alternate return circuit can be included on, or adjacent to the ablator, such that the return circuit is be on the same side of the ablator with respect to the atrial wall. The return circuit typically defines a greater distance from the ablator than the thickness of the target tissue in order to maximize the likelihood that a full thickness ablation is achieved. Another option can be to place a return electrode on the epicardial (outside) surface of the heart. The option of placing the return electrode across from the ablator, is often desirable in terms of the electrical characteristics of the system, as the energy is significantly focused and applied in a highly efficient manner. An optional return circuit can include an electrode on a minimally invasive device to be inserted into and mounted on or located near (proximate to) the wall of the esophagus, adjacent to the heart. Since this can be applied with standard minimally invasive devices, and yields a relatively short electrical path, it can be a desirable method of applying ablation energy. Illustratively, the electrode can reside in the lumen of the esophagus, or can be attached to the wall of the esophagus, using an anchoring system similar to that proposed for the anchor in the pulmonary vein.

As a further feature of the apparatus and method, during catheter ablation procedures, Transesophageal Echocardiographic (TEE) Ultrasound is often used as a guidance tool for placing the ablator. The TEE instrument can also include an electrode for the return ablation energy circuit as described above. A minimally invasive device inserted into the esophagus can also contain one or more magnets, in which opposite-pole magnets can be included in the ablator device. Thus the TEE device can include magnets to enhance, or provide, the prime anchoring technique for holding the ablator against the target.

BRIEF DESCRIPTION OF THE DRAWINGS

The invention description below refers to the accompanying drawings, of which:

FIG. 1A is a side view of a point ablator including a balloon anchor with discrete point ablator catheter, in accordance with an illustrative embodiment;

FIG. 1B is a front view of the compass ablator according to the illustrative embodiment;

FIG. 2A is a cross-sectional view of the catheter and associated sheath for a catheter, having two steering cables, and optional guide catheter lumen, according to the illustrative embodiments;

FIG. 2B is a cross-sectional view as taken through the catheter and associated sheath for a catheter, having four steering cables, and optional guide catheter lumen, according to the illustrative embodiments;

FIG. 3A is a side view of an anchor umbrella and ablator umbrella shown in the stored position, according to the illustrative embodiments;

FIG. 3B is a detailed side view of the strut details, according to the illustrative embodiments;

FIG. 4A is a side view of the anchor umbrella and ablator umbrella, shown in the deployed position, according to the illustrative embodiments;

FIG. 4B is a front view of the anchor umbrella and the ablator umbrella, shown in the deployed position, according to the illustrative embodiments;

FIG. 7A is a side view of a balloon anchor and a balloon ablator, shown in the deployed position, according to an illustrative embodiment;

FIG. 7B is a front view of the balloon anchor and the balloon ablator, shown in the deployed position, according to the illustrative embodiments;

FIG. 8 is a side view of an umbrella anchor and an umbrella ablator cinch mechanism operatively connected to a helix drive, according to an illustrative embodiment;

FIG. 11A is a side view of a separated mushroom-balloon anchor having non-occluding ribs and an ablator balloon, according to an illustrative embodiment;

FIG. 11B is a detailed cross-sectional view as taken through the line 11-11 of FIG. 11A, according to the illustrative embodiments;

FIG. 11C is a front view of the ablator balloon, according to the illustrative embodiments;

FIG. 12A is a side view of an umbrella anchor and an annular balloon ablator, according to an illustrative embodiment;

FIG. 12B is a front view of the annular balloon ablator, according to the illustrative embodiment;

FIG. 14 is a perspective view of an umbrella ablator and mushroom anchor in place in the left superior pulmonary vein, in the left atrium of a patient, according to the illustrative embodiments;

FIG. 15 is a perspective view of the resulting ablations in the left atrium, according to the illustrative embodiments;

DETAILED DESCRIPTION

Figure 5A:
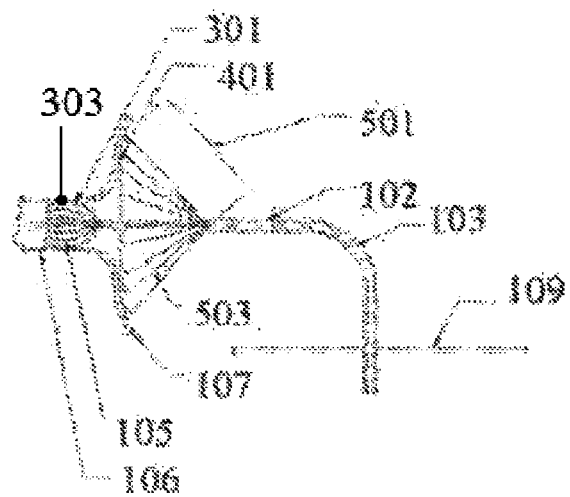
FIG. 5A is a side view of the anchor umbrella and an ablator pinwheel, shown in the deployed position, according to an illustrative embodiment.

An apparatus and method for performing cardiac ablation employs a catheter and various anchoring and ablation techniques, according to illustrative embodiments described herein. The various arrangements and types of apparatus components are shown in the illustrative embodiments of FIGS. 1-18.

A. Catheter Including Balloon Anchor and Compass Ablator

Reference is now made to FIGS. 1A and 1B showing, respectively, a side and front view of an illustrative embodiment of a cardiac ablation catheter comprising a point or "compass" ablator and balloon anchor. The point ablator is maneuvered circumferentially similar to a compass, thereby this embodiment is referred to as a compass ablator 100 includes a balloon anchor 101 at the distal tip 110 of the catheter 103. An "anchor", as the term is used generally herein, refers to the structure assembled on a distal end of the catheter for application within the pulmonary vein. The anchor structure expands radially outwardly so as to contact the pulmonary vein wall. The catheter as generally used herein refers to a catheter having an external diameter of approximately 12 French (F), which can be more or less depending on the particular application and includes lumens and conductors as appropriate for the particular application as described herein.

The catheter 103 includes a protective outer sheath with lumen 102. Proximal to the anchor 101 is a point ablation catheter 104 emanating radially at an angle from the midcath 103 to contact the atrial wall 107 around the pulmonary vein 106. This is the catheter that is used during the ablation phase. A pacing catheter 108 is disposed proximal to the point ablation catheter 104. The pacing catheter 108 is arranged to contact the atrial wall tissue 107 radially outside the ablation line. By emitting an electrical signal from the pacing catheter 108, the electrical contact on the anchor detects the pacing signal if the ablation line is incomplete. The term "ablator" as used herein refers broadly to the structure assembled proximal to the anchor and onto the catheter, having a circumferential configuration so as to surround the tissue surrounding the pulmonary wall. The ablator can be any appropriate shape and use any of a variety of modalities (or combination of modalities, such as resistance heating, RF, ultrasound, etc.) to perform ablation of internal tissue. Moreover, the ablator configuration can be constructed and arranged to define any shape that is suitable for use in conjunction with the pulmonary vein opening, as described in greater detail hereinbelow.

The anchor 101 provides stabilization to the ablator 100 for this and other embodiments described herein. The stabilization effect provided allows physicians and/or other clinicians to utilize a standard "off-the-shelf" point ablator while maintaining the various advantages described herein. The anchor also allows a user to have more control of the point ablator contact because the catheter is anchored within a desired portion of the heart and ablation can be targeted more specifically. The anchor moreover allows for additional linear ablation lesion lines such as a roof line (shown in FIGS. 16 and 17) or other ablation techniques known to those having ordinary skill.

B. General Catheter Structure

Reference is made to FIGS. 2A and 2B showing a cross-sectional view as taken through the catheter 103 of FIG. 1 and other embodiments of the catheter shown and described herein. FIGS. 2A and 2B show the catheter 103a, 103b having an outer lumen 102 with an outer diameter D1 of approximately 0.158 inches in an illustrative embodiment. The inner diameter D2 of the outer lumen 102 is approximately 0.128 inches and the outer diameter D3 of the catheter 103a, 103b is approximately 0.125 inches. These measurements are for illustrative purposes to provide an exemplary embodiment and are highly variable within the scope of ordinary skill. These sizes can be used in the various embodiments as described herein.

FIG. 2A shows a catheter 103a having two steering cables according to an illustrative embodiment. The catheter 103a includes conventional fluid lumens 201 and provides the two depicted steering cables 202 for steering the catheter as it is manipulated through the body/vasculature to reach a destination. The cathether 103a of FIG. 2A includes illustrative conductors 203 appropriately positioned to allow for the elements of the catheter to be disposed therein. A lumen to accommodate a guide catheter 204, as an option is described in greater detail herein, is also provided. The positioning of such catheter elements, and numbers of each type of element within the catheter is highly variable, as will be readily apparent to those having ordinary skill.

FIG. 2B shows an illustrative catheter 103b having four steering cables. The catheter 103b of FIG. 2B includes conventional fluid lumens 201 and four steering cables 202. The conductors 203 are also provided in the catheter to provide the appropriate connectivity for electrical signals that perform ablations. A lumen to accommodate a guide catheter 204 an option for the catheter is also provided, as is described in greater detail hereinbelow.

C. Catheter Including Umbrella Anchor and Umbrella Ablator

An embodiment employing an illustrative umbrella anchor and umbrella ablator is shown in FIGS. 3A, 3B, 4A and 4B. As shown in the side view of FIG. 3A and the front view of FIG. 3B, the umbrella anchor 301 is shown deployed in the pulmonary vein and the umbrella ablator 302 is shown in the stored position. The umbrella anchor and umbrella ablator in one embodiment can be opened passively by being fabricated from shape-memory materials such as certain aluminum alloys, nitinol or another appropriate metal, or yet other appropriate materials/structures. In another embodiment, the anchor and/or ablator can be positively actuated to the deployed position, rather than attaining this position via the spring action of a memory material. In a stored position the anchor/ablator according to various embodiments reside and are packaged within, or on, a catheter under a sheath so as to allow for passage from an entry port to the left atrium. Once located at the desired position, the outer sheath is withdrawn or pulled proximally (see arrow A3), to expose the umbrella ablator 302 and allow it to expand to its deployed position as shown in FIGS. 4A and 4B. Note that although the outer sheath 102 is withdrawn (or retracted/pulled/moved) in FIG. 3A and shows the umbrella ablator 302 in the stored position, in operation as the sheath 102 is withdrawn, it causes the umbrella ablator 302 to expand concurrently in embodiments constructed from a shape memory alloy. It is shown in the stored position with the sheath retracted for illustrative and descriptive purposes. This embodiment provides a manual control for activation of the umbrella ablator. Various other embodiments, which include automated activation mechanisms or electric actuators for deploying the ablator, are described and shown herein.

The anchor is opened to an expansion of the pulmonary vein based on the radial force of the anchor against the pulmonary vein wall. The force measurement can be achieved illustratively by one or more micro force sensors 303 mounted on the struts of the anchor. By way of example, one such force sensor can be a microstrain gauge. This form of gauge directly measures the radial expansion force. A second indirect optional force measurement can be achieved by measuring the tensile force on the cinch cable (as shown in FIG. 8).

FIG. 3B shows a representation of a strut for an ablator. The umbrella ablator 302 is stored within the catheter 103 and consists of an array of struts 312 with an ablation circuit 306 on one side so it will contact the tissue at the tissue interface. An electrically insulative material 305 is applied between the ablation circuit 306 and feedback circuit 310. The details of struts 312 can also be provided for the umbrella ablator struts that are described herein.

The umbrella anchor 201 is shown as an open-end, stent-like device. It can have an electrical feedback circuit (not shown) contacting the tissue. A single force sensor (not shown) can be included, for example in the umbrella ring 313, to detect and send axial compression force between the umbrella 302 and anchor 201. Alternatively, force sensors located on each strut, not shown, but as part of a feedback circuit can be included to detect force at each ablator electrode.

FIGS. 4A and 4B show, respectively, side and front views of the umbrella anchor 301 and umbrella ablator 302 in the deployed position. Ablation occurs when power is emitted through the ablator circuit 401 to the target tissue, such as an atrial wall 107. A separate return circuit can be deployed and energy can return through an electrode placed in the esophagus (not shown here, but refer to FIGS. 13A and 13B for a TEE anchoring system). A return electrode can also be included in the umbrella or can be deployed on heart tissue beyond/outside the circumference of the ablation line. Conduction is measured across the ablation lines via electrodes (not shown) that contact outside the ablation ring (similar to the strut construction in FIG. 3B) and 105 (inside the ablation ring). Acceptance criteria is based upon catheter data collections and observations. If power requirements preclude ablation through an entire circumferential ablator, one or more segments can be ablated through a device similar to the ablator pinwheel structure 502 of FIG. 5B and other ablators as described herein. Upon completion of a first ablation step, the entire ablator (for example ablator 302 of FIGS. 4A and 4B) can be rotated about the axis of the anchor in place in the pulmonary vein 106. Rotation of the ablator occurs such that previous ablation overlaps each subsequent ablation. Refer to FIG. 15, described hereinbelow, for a perspective view of the resulting ablations in the left atrium of a patient, in accordance with the various illustrative embodiments herein.

The umbrella anchor 301 of FIGS. 3A, 3B, 4A and 4B, and other embodiments described herein, desirably provides stability for the ablator, and allows the umbrella ablator to be cinched down or compressed against the posterior atrial wall around the pulmonary vein. Notably, the umbrella anchor allows blood to flow therethrough during the ablation phase with negligible obstruction. The umbrella ablator further allows the ablator structure and in particular its conducting electrode surface to maintain contact with the atrial wall 107 during the ablation phase, thereby providing a stable base for performing the ablation.

D. Catheter Including Umbrella Anchor and Pinwheel Ablator

Figure 5B:
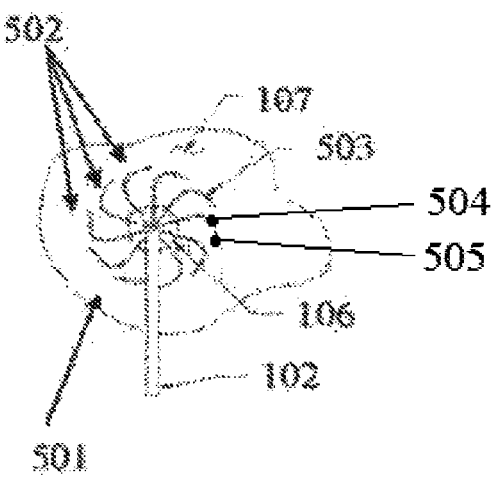
FIG. 5B is a front view of the anchor umbrella and the ablator pinwheel, shown in the deployed position, according to the illustrative embodiments.

Reference is now made to FIGS. 5A and 5B showing, respectively, a side and front view of an umbrella anchor 301 and a pinwheel ablator 501 shown in the deployed position. When in the stored position, the structure resembles the catheter structure of FIGS. 3A and 3B. As depicted in FIGS. 5A and 5B, each strut 502 of the pinwheel ablator 501 is separate from adjacent struts 502. Each strut, as the conductor between the driving circuit and target tissue, has an electrode 505 which is to be positioned in intimate contact with the target tissue. Each strut 502 of the pinwheel ablator 501 also defines a compound curve 503 of appropriate arrangement to provide the desired overall structure for, and positioning of the electrode surface against the tissue in preparation for ablation. The struts 502 of the pinwheel 501 can be constructed from a memory metal wire, or another appropriate material. The number of struts 502 on the pinwheel 501 is highly variable to achieve the desired circumference for ablation. The struts are aligned sufficiently close together circumferentially, in order to provide overlapping ablation energy with respect to each adjacent electrode thereby creating a continuous ablation line. In the event that any ablation line formed by the device is not continuous, the ablator can be pulled slightly distally, rotated and reseated to create an overlapping ablation segment.

The umbrella anchor 301 allows blood to flow therethrough during ablation and provides a structural surface for electrical contact for a feedback circuit. The discrete ablator struts 502 of the pinwheel ablator 501 allow for each strut to have a distinct electrode to conform to the rough topography of the atrial surface 107. A micro force sensor 504 mounted on each electrode pad can insure that each electrode is in sufficient contact, or that the particular electrode is not used in the ablation process. In addition, impedance and/or current measurement through each ablation electrode can provide a significant source of additional feedback to determine if each electrode is in sufficient contact to allow it to be used in the ablation. The discrete ablator electrodes for each ablator strut 502 are also readily stored within the catheter when in the stored position.

E. Catheter Including Mushroom Anchor and Umbrella Ablator

Figure 6A:
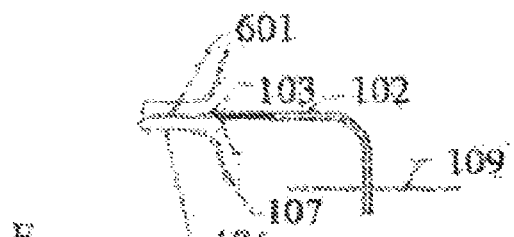
FIG. 6A is a side view of a mushroom anchor and an ablator umbrella, shown in the stored position, according to an illustrative embodiment.
Figure 6B:
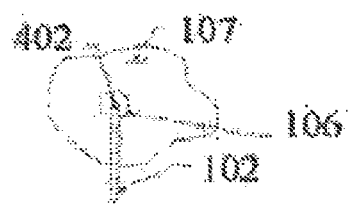
FIG. 6B is a front view of the mushroom anchor and the ablator umbrella, shown in the stored position, according to the illustrative embodiments.
Figure 6C:
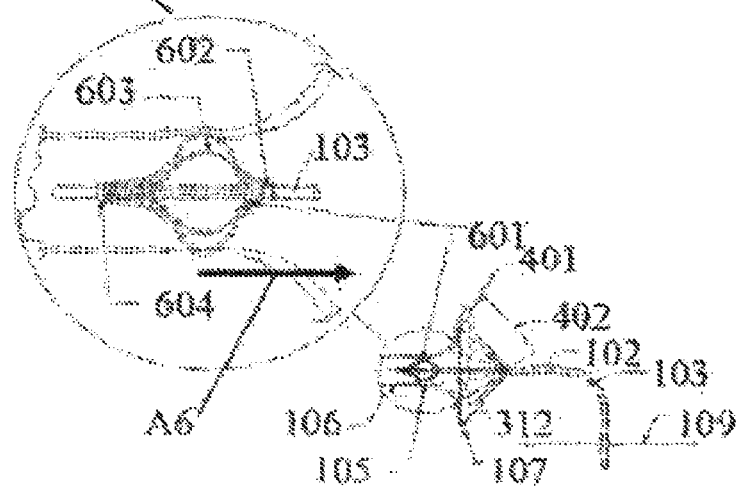
FIG. 6C is a side view of the mushroom anchor and the ablator umbrella, shown in the deployed position, according to the illustrative embodiments.
Figure 6D:
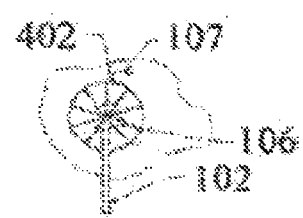
FIG. 6D is a front view of the mushroom anchor and the ablator umbrella, shown in the deployed position, according to the illustrative embodiments.

Reference is now made to FIGS. 6A-6E showing an active mechanism to deploy an umbrella that incorporates a mushroom anchor 601 according to an illustrative embodiment. Other active mechanisms for umbrella deployment can include electro-actuators, shape-memory alloy, piezoelectric or similar technology and materials. FIGS. 6A and 6B show, respectively, side and front views of the mushroom anchor in the stored position. FIGS. 6C and 6D show, respectively, side and front views of the mushroom anchor and umbrella ablator in the deployed position. As depicted in the detail 'E' of FIG. 6C, the mushroom anchor includes spring struts 603 that are rigidly supported on a proximal support ring 602 and a distal support ring 604. According to the illustrative embodiment, the proximal ring 602 is fixed and the distal ring 604 of the mushroom anchor 601 can be moved proximally (see arrow A6) and the spring struts 603 are compressed. Alternate arrangements for fixation of the ring to provide compression of the struts are expressly contemplated and should be apparent to those having ordinary skill. For example, the distal ring can be fixed and the proximal ring can be movable, or both rings can be movable relative to each other to provide for the desired movement characteristic for the struts. The spring struts 603 can have a pre-set bend which are activated upon proximal movement of the distal ring 604 of the mushroom anchor 601. Actuated movement in both directions of one or both of the rings 602 and 604 can be desirable to insure enhanced control and proper closure of the anchor during removal, prior to reinserting the inner sheath over the anchor.

The mushroom anchor 601 allows blood to flow therethrough during the ablation phase, and any time proximate thereto. The mushroom anchor is secured by rings or other appropriate structures to provide sufficient rigidity, while allowing the distal end of the anchor to be moved proximally, or the proximal end to be slid/advanced distally, thereby providing a controlled radial expansion of the anchor against the pulmonary vein wall. Force sensors, such as microstrain gauges (not shown), located on at least one strut, and/or optionally mounted on pairs of diametrically opposing struts can be included.

H. Catheter Including Balloon Anchor and Balloon Ablator

Reference is now made to FIG. 7A showing a side view of a balloon anchor and balloon ablator according to an illustrative embodiment. As shown, the balloon anchor 701 is inserted into the pulmonary vein 106. When in the desired position, the balloon anchor 701 is expanded until it contacts the pulmonary vein wall 106 sufficiently to maintain its position within the vein as shown in FIG. 7A. The balloon ablator 702 is then also expanded to its desired size. The balloon ablator 702 is then advanced distally (arrow A7) until its conduction block circuit 705 (shown in FIG. 7B, as taken through line 7-7 of FIG. 7A) and ablation circuit 706 contact the atrial wall 107. The balloon anchor 701 and balloon ablator 702 can be expanded and/or activated by pumping a bio-compatible fluid (e.g. saline solution), or other safe working material into each balloon chamber as desired. Balloon pressure measurement can be used analogous to force measurement to relate that pressure to anchor retaining force or ablation compression force, as known to those having ordinary skill. The balloon ablator 702 and balloon anchor 701 can be more conformable to the patient's atrial topography than conventional strut devices, and also provide wider load distribution against the adjacent tissue. Additionally, the balloons can be readily constructed according to conventional techniques and easily stored within the catheter.

I. Catheter Including Umbrella Anchor and Umbrella Ablator

Referring now to FIG. 8, an umbrella anchor 301 and umbrella ablator 302 are shown further including a cinch mechanism according to an illustrative embodiment. As shown, a cinch cable 803 is connected to the umbrella ablator ring mount (UARM) 313 and passes through a pulley 804 on the anchor ring mount (ARM) 801 back to a helical drive mechanism 802 on the external control device (not shown). Turning the helix drive mechanism 802 exerts tension on the cable 803, and allows the ablator 302 to be compressed against the target tissue on the atrial wall 107. Other forms of mechanisms (not shown) can include a mini-helical drive within the catheter from which the ablator can be advanced, as commonly applied by those having ordinary skill. A linear slide and catch drive mechanism, although not shown, is another ablator compression mechanism, known commonly in the art as a "Quick-Grip bar" or a Clamp mechanism. The cinch mechanism of FIG. 8 allows the ablator to be moved or compressed against the target tissue according to an illustrative embodiment.

Figure 9A:
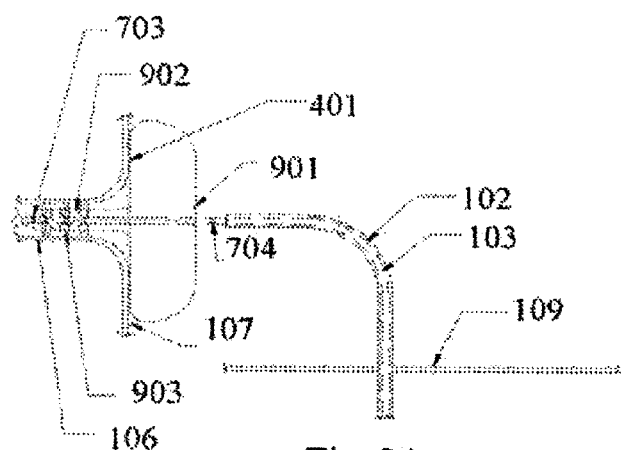
FIG. 9A is a side view of a combination mushroom and balloon anchor having ribs and an ablator balloon, according to an illustrative embodiment.
Figure 9B:
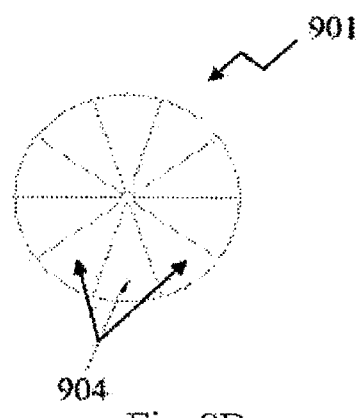
FIG. 9B is a front view of the ablator balloon according to the illustrative embodiment.

J. Catheter Including a Combination Mushroom Balloon Anchor and Mushroom Balloon Ablator Reference is now made to FIGS. 9A and 9B showing, respectively, a side and front view of a combination mushroom and balloon anchor having non-occluding ribs and a balloon ablator, according to an illustrative embodiment. The mushroom balloon anchor 902 and mushroom balloon ablator 901 are combined into a single structure, as shown in FIG. 9A. Once the anchor is properly set, the balloon expansion will compress its distal surface with the ablator and conduction block circuits against the atrial wall 107. The mushroom balloon anchor 902 and combined ablator 901 includes segmented sections 904 so that each section can independently contact tissue and slide with respect to adjacent sections. Bypass holes 703 and 704 are provided which allow blood to continue to flow through the pulmonary vein during the combination mushroom balloon anchor occlusion of the vein during the ablation phase. The size of the bypass holes is highly variable.

Figure 10A:
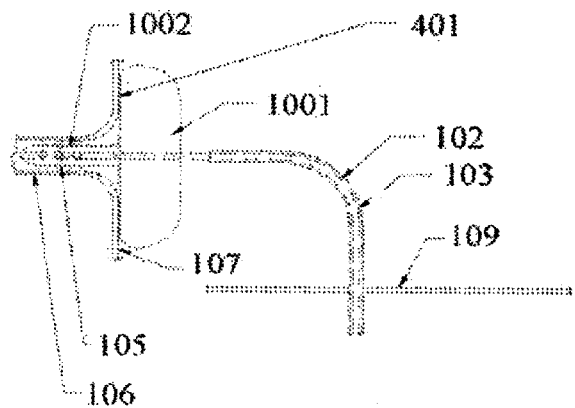
FIG. 10A is a side view of a combination mushroom and balloon anchor having non-occluding ribs and a balloon ablator, according to an illustrative embodiment.
Figure 10B:
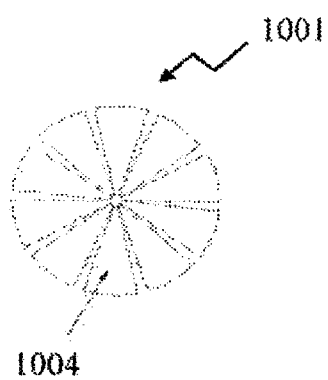
FIG. 10B is a front view of a segmented ablator balloon, according to the illustrative embodiment.

K. Catheter Including a Combination Mushroom Balloon Anchor and Mushroom Balloon Ablator Having Separated Segments FIGS. 10A and 10B show, respectively, a side view and a front view of a combination mushroom balloon anchor 1002 and ablator 1001, according to an illustrative embodiment. As shown in FIG. 10B, the mushroom balloon ablator 1001 includes separated segments 1004 that allows for each section to contact tissue independently. The segmented anchor balloon allows blood to flow therethrough during the ablation phase, which lessens the occlusion effect of conventional balloon procedures. The segmented balloon also provides localized contact against the atrial posterior wall. Turning the ablator balloon 1001 about the axis of the anchor balloon 1002 generates a continuous circumferential ablation (as shown in FIG. 15 as ablations 1510, for example). Bypass holes 703 and 704, (see for example FIG. 7A), can be included to provide bloodflow therethrough when inflated.

L. Catheter Including a Mushroom Balloon Anchor Separated from a Balloon Anchor

Referring to FIG. 11A, a separated mushroom balloon anchor with non-occluding ribs and mushroom balloon ablator is shown according to an illustrative embodiment. The anchor balloon 1101, as shown in greater detail in FIG. 11B as taken through line 11-11 of FIG. 11A, includes non-occluding ribs, and is separated from the mushroom balloon ablator. The balloon anchor 1101 is inserted and inflated within the pulmonary vein 106. Once sufficiently inflated to maintain position, the balloon ablator 702 is inflated. The balloon ablator is then compressed against the atrial wall 107. Bypass holes can be included for allowing blood to flow therethrough. The separated mushroom balloon ablator allows for full contact of the ablator with the target tissue. Also, the separated mushroom balloon provides localized contact against the atrial posterior wall, similar to the struts 502 in the pinwheel structure.

M. Catheter Including an Umbrella Anchor and Annular Balloon Ablator

Reference is now made to FIG. 12A showing a side view of an umbrella anchor 301 and an annular ablator balloon 1201 having a unique annular ring. The annular ring includes circuits 401 on its surface, protruding distally toward the atrial wall 107. The conductor circuits 401 include the ablator circuit 1202, conduction block circuit 1203 and an optional force sensor circuit (not shown). In operation, the circuits 401 are compressed against the target tissue of the atrial wall 107. The combination umbrella anchor with annular balloon ablator allows full and targeted contact of the ablator with the target tissue and in the ostium vascular system (vs) at the pulmonary vein. The contour of the annular balloon ablator includes the boss-like ring features that provide full contact with the target tissue.

O. Magnetic Anchor as Part of a Transesophageal Device

Figure 13A:
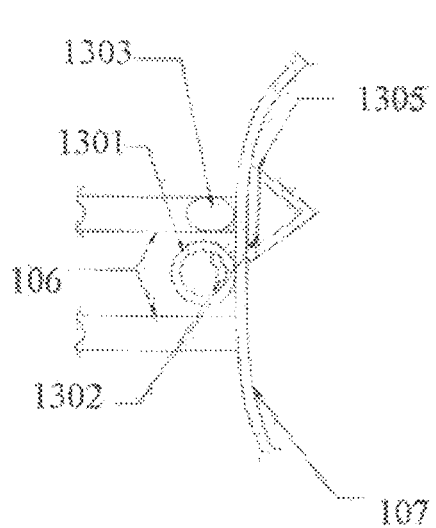
FIG. 13A is a side view of a magnet anchor as part of a transesophageal echocardiogram (TEE), according to an illustrative embodiment.
Figure 13B:
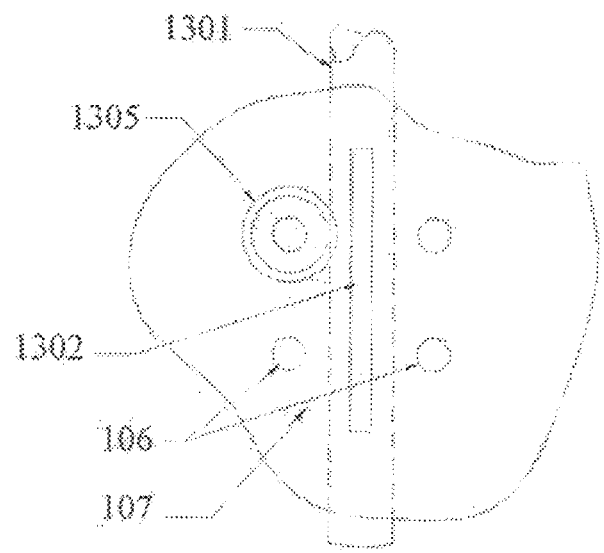
FIG. 13B is a front view of the magnet anchor as part of the TEE, according to the illustrative embodiment.

Reference is now made to FIGS. 13A and 13B showing, respectively, a side and front view of a magnet anchor as part of a transesophageal echocardiogram (TEE), according to an illustrative embodiment. One or more magnets 1302 are included in an instrument located proximate an esophagus 1301. The magnets 1302 provide sufficient force to anchor the ablator return circuit 1305 in position with respect to the pulmonary vein 106. Additional anchors can also be provided to improve the overall anchoring effect including use of a balloon anchor, umbrella anchor, or other structures as described herein. The illustrative magnetic anchors 1302 provide a holding mechanism opposing the ablator. Ablator return circuit 1305 provides a directly transmurally opposing (i.e. through the wall) return circuit, which optimizes the ablation field and thereby provides effective ablation.

P. Medical Treatment Procedure for Cardial Ablation

Figure 14A:
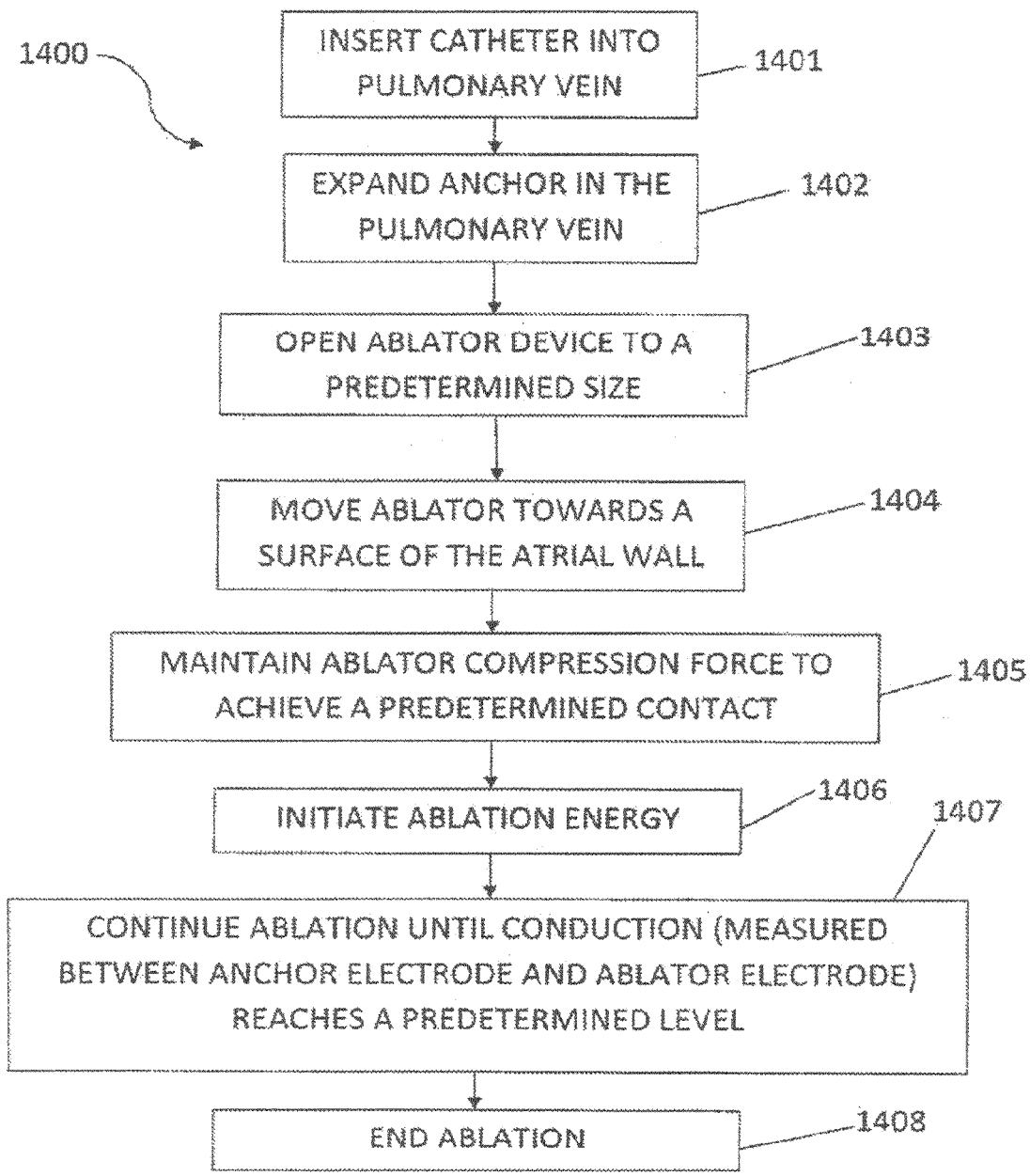
FIG. 14A is a flow chart of a procedure for performing an anchored cardiac ablation, according to an illustrative embodiment.

Reference is made to FIG. 14A showing a flow chart of a medical treatment method or procedure for performing an anchored cardiac ablation, according to an illustrative embodiment. At step 1401 the procedure initiates when a catheter is inserted into the pulmonary vein. The catheter reaches the pulmonary vein by being steered into the right atrium. A transseptal puncture is then created through the septal wall dividing the two atria or upper chambers in the heart. The catheter (or guide catheter) is advanced into a pulmonary vein. Once the catheter is at the desired location, inner sheath is pulled proximally. The anchor of the catheter is expanded into the pulmonary vein at step 1402 against the pulmonary vein to a predetermined force as measured by a micro force sensor. Then at step 1403, the ablator device is opened to a predetermined size and then it is moved towards a surface of the atrial wall at step 1404. The ablator compression force is then maintained at step 1405 to achieve a predetermined contact, as measured by a micro force sensor, with the desired tissue surface. Each electrode's pad contact is measured via the force measurement and/or via a conduction and/or impedance measurement. At step 1406 ablation energy is initiated to commence ablation of the desired target tissue. Ablation continues at step 1407 until conduction feedback reaches a predetermined level. The conduction is measured across the ablation line between an anchor electrode and an ablator conduction measurement electrode, according to conventional techniques. Once the predetermined level of conduction is reached, the ablation ends at step 1408. Once ablation is complete, the ablator is collapsed into its stored position configuration and pulled within the outer sheath. The anchor is then collapsed to its stored position configuration and pulled within its inner sheath. The illustrative CircumBlator Catheter of the embodiments shown and described is pulled withdrawn out of the pulmonary vein just ablated and moved into a second pulmonary vein to repeat the process until all four pulmonary veins are completely ablated.

Q. Operational Embodiment

Figure 16:
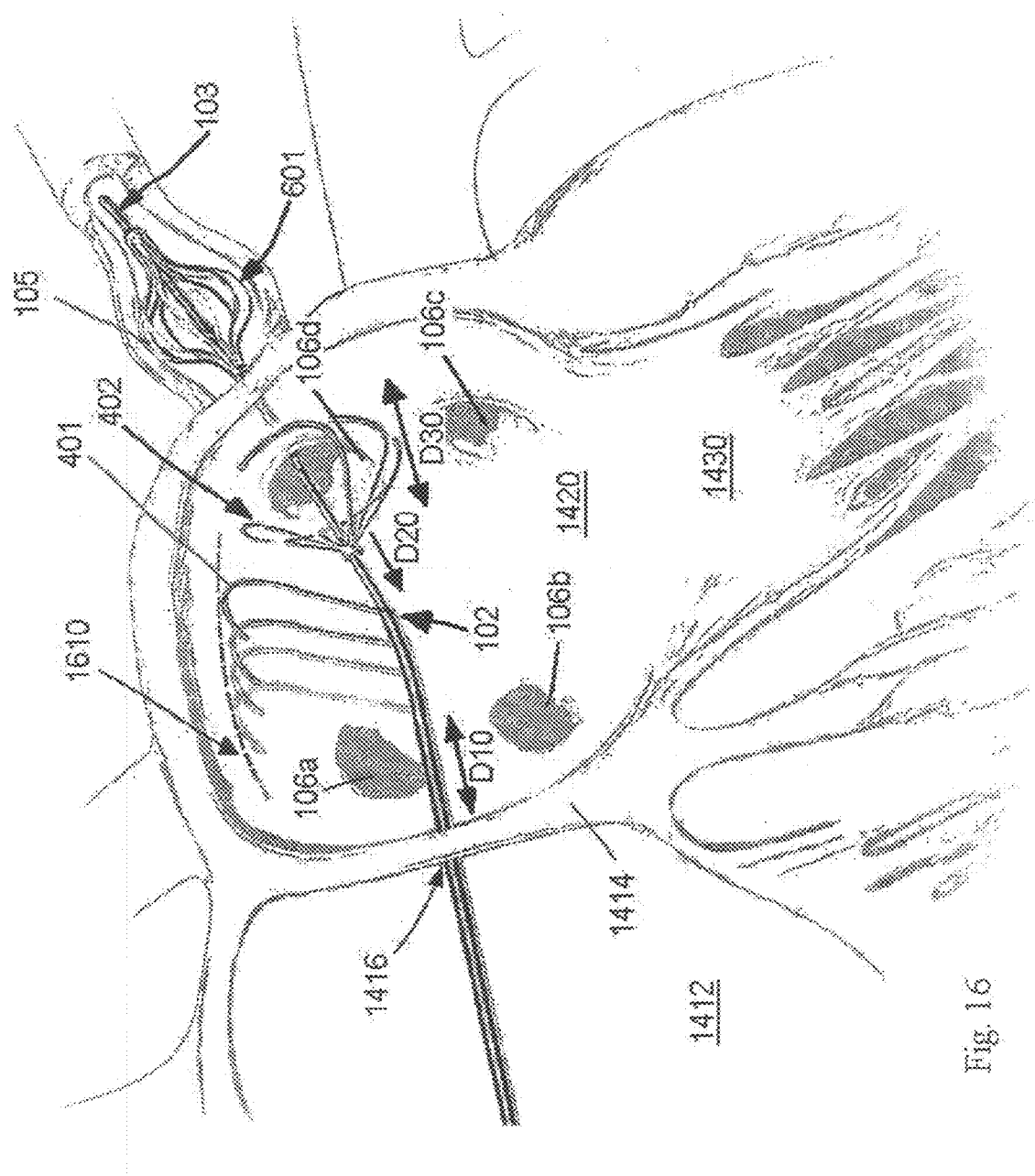
FIG. 16 is a perspective view of the umbrella ablator and mushroom anchor, and further performing a roofline ablation, according to an illustrative embodiment.
Figure 17:
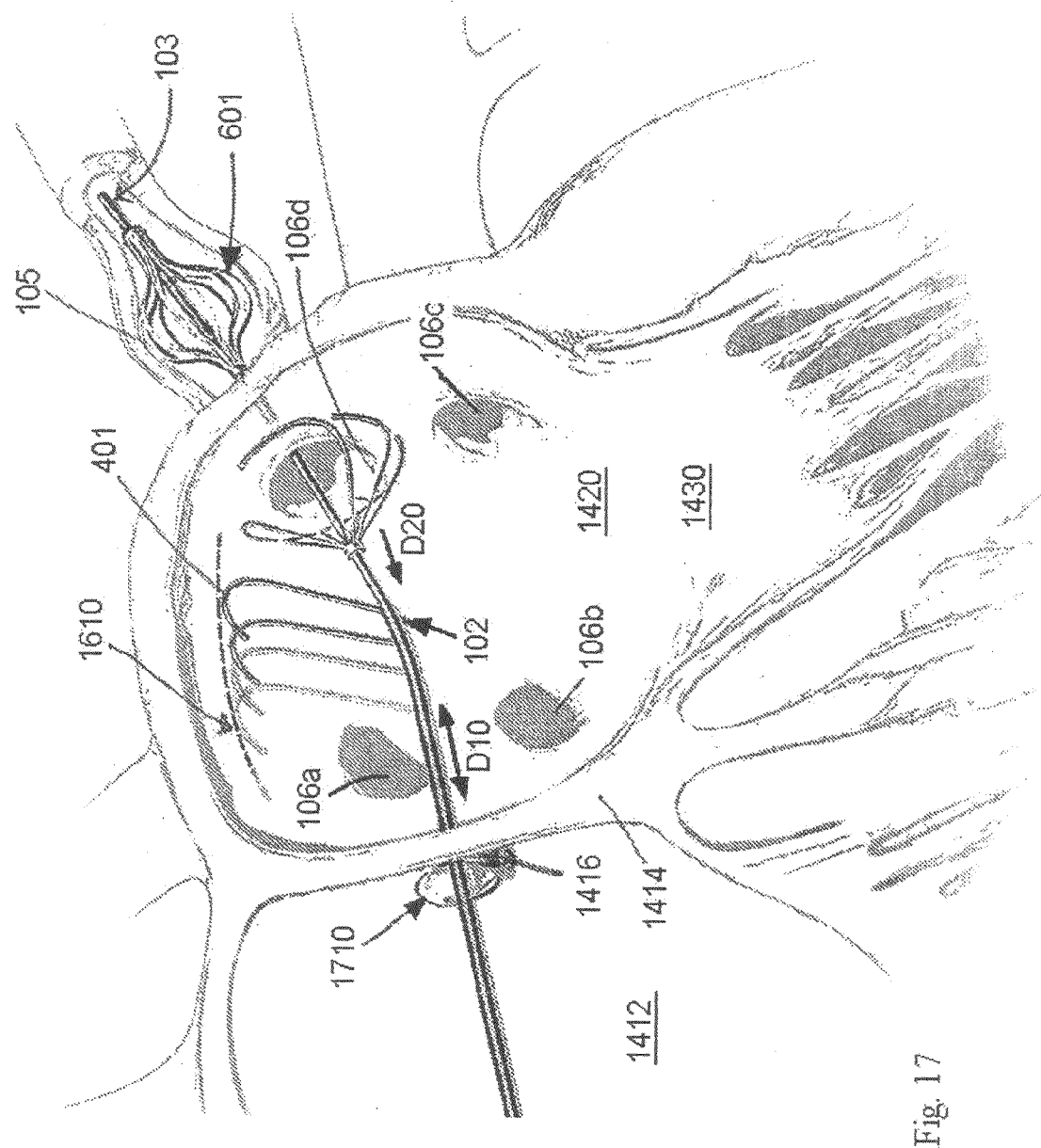
FIG. 17 is a perspective view of the umbrella ablator and mushroom anchor, further including a balloon support for the catheter, according to the illustrative embodiments.

An operational embodiment employing an umbrella ablator and a mushroom anchor is shown in FIGS. 14-17, showing perspective views of a heart of a patient undergoing cardiac ablation in accordance with the various illustrative embodiments described herein, with FIG. 15 depicting the resulting ablations. Referring to FIGS. 14, 16 and 17, the tip of the catheter 103 with outer sheath 102 reaches the left atrium 1420 according to standard techniques, entering the right atrium 1412 through, for example, the femoral vein and the inferior vena cava. The catheter 103 then penetrates the septum 1414 via a trans-septal puncture 1416 between the left and right sides of the heart and enters into the left atrium 1420. Once inserted into the pulmonary vein 106*d*, the anchor 601 is deployed. The anchor expands until a radial wall force is reached, which can be detected by a sensor or other sensing device incorporated into the anchor. Although a mushroom anchor 601 and umbrella ablator 402 are shown in these operational embodiments, any anchoring technique and ablating device as contemplated herein can be employed. An illustrative force sensor 105, 903 allows measurement of the force of the anchor 601 on the pulmonary vein 106*d* wall. This measurement step performs two functions, one to minimize chance of vessel rupture, and the other is to ensure the application of sufficient radial wall force to ensure the anchor remains in place minimizing axial motion with respect to the pulmonary vein. The anchor should then be pulled distally towards the atrium to seat the anchor both radially against the wall and axially against the atrial wall-pulmonary vein intersect.

Once the anchor is determined to be in place, the ablator umbrella 402 (or point ablator or balloon ablator of other embodiments) expands until it reaches a predetermined position. The umbrella ablator (or balloon ablator described herein) is advanced until it sufficiently compresses against the target atrial tissue, as shown in full contact in FIG. 14. The ablation phase occurs by performing an ablation with one or more electrodes. If necessary electrode 401 rotating the ablator may be required to complete a continuous ablation ring. The ablation can be performed for each pulmonary vein (106*a*, 106*b*, 106*c*, and 106*d*), and results in the depicted ablations 1510, which are shown in FIG. 15. Ideally, the ablations define a predetermined pattern, such as the depicted ring 1510.

Referring to FIG. 16, the anchor is shown seated within a Pulmonary Vein (PV), and the umbrella ablator remains cinched against the atrial posterior wall. In the ostial area around the same PV, one electrode 401 is used as a linear ablator. The electrode 401 that is used to ablate linear lesions, constructed like a guide catheter with steering wires, is refracted proximally into the outer sheath from the umbrella ablator. The outer sheath 102 is refracted proximally (direction of arrow D10), away from the umbrella ablator and towards the trans-septal puncture 1416 to a desired position. The electrode 401 that is used to ablate linear lesions, constructed as a guide catheter with steering wires, is refracted proximally into the outer sheath from the umbrella ablator. When the outer sheath 102 is retracted to a desired position (arrow $D_2O$) and locked in place, the electrode ablator can then be advanced out beyond the distal end of the sheath, and steered towards the target tissue. Once the electrode ablator is adjacent to the target, the Electrophysiologist (EP) (or other practitioner) rotates the elongated pad segment of the electrode so it is oriented in the path of the line to be ablated. Then the EP illustratively pushes and compresses the electrode pad against the tissue and ablates (arrow D30). The force sensor and current/impedance feedback provides information about the lesion creation. Standard mapping techniques are desirable employed to monitor the ablation position as each location is ablated in turn.

In another embodiment, with the anchor seated within a Pulmonary Vein (PV), the umbrella ablator can be moved/withdrawn proximally, away from the PV, and towards the trans-septal puncture. It may or may not be pulled back into its outer sheath. When the umbrella ablator is positioned in a desired location, between the PV at the distal end and the trans-septal puncture at the proximal end, one electrode is extended distally (arrow $D_2O$) and steered towards the target tissue. Once the electrode ablator is adjacent to the target, the Electrophysiologist (EP) rotates the elongated pad segment of the electrode so it is oriented in the path of the line to be ablated. Then the EP pushes and compresses the electrode pad against the tissue and ablates (arrow D30). The force sensor and current/impedance feedback provides information about the lesion creation.

Once the electrode 401 ablates a first line segment, the electrode 401 (and/or the outer sheath 102) is moved parallel with and just beyond one end of the already ablated line segment. Once properly aligned the next segment is ablated, overlapping it with the prior segment. This procedure is repeated until the entire length or segment of the line is completed or achieves the desired predetermined pattern and/or electrical measurement.

Once a Pulmonary Vein is isolated and the neighboring segment of the linear lesion is completed, the umbrella ablator 402 is withdrawn back into its outer sheath (such withdrawal can have occurred at a previous time), the anchor 601 is collapsed and retracted into its inner sheath, the anchor 601 and guide catheter 103 is withdrawn from the PV and inserted into the next PV. The above-described insertion process and subsequent withdraw is then repeated until the overall medical treatment is complete.

With reference to FIG. 16, to create a roof line 1610 each half of this line is generated when the anchor was seated in the right superior pulmonary vein (RSPV) 106*a* and left superior pulmonary vein (LSPV) 106*d*. In addition to creating the roof line ablations, the ablator can perform other adjacent linear ablations. It should be readily apparent to those having ordinary skill that the ablators as shown and described herein can perform any linear ablations in the left atrium.

To create the line to the mitral annulus 1430 from the roof line (not shown), the upper portion of the line is made with the anchor seated in one of the upper pulmonary veins and the other portion with the anchor seated in one of the right lower pulmonary vein (RIPV) 106b and left lower pulmonary vein (LIPV) 106c.

One or more electrodes of the umbrella ablator can be steerable, in accordance with the illustrative embodiments. In an embodiment, if only one electrode is steerable, then the catheter can be rotated to properly position that electrode with respect to the target location. If there is sufficient space, two electrodes can be provided with steerability, and are constructed illustratively in an arrangement in which each electrode is diametrically opposed within the catheter.

The arrangement of FIG. 16 allows one device, the umbrella ablator, to ablate both PVI, and one or more of its electrodes can be employed to create a continuous linear ablation with a series of overlapping line segments. This structure allows the umbrella anchor to be stabilized at the pulmonary vein, along with the catheter acting as a platform from which the electrodes can be advanced radially away from the catheter to create the linear ablations. The catheter platform provides a stable base from which to ablate and provides stable contact as compared to prior art stand-alone point ablators. This makes the entire procedure readily reproducible and quicker for EPs to achieve the predetermined ablation pattern.

Another option for performing ablations, although not shown, is to remove the umbrella ablator and insert a standard point ablator. This can be an RF or cryoablator, depending on the preference of the EP. It is inserted along the guide catheter part way into the left atrium. At a desired position the EP steers the point ablator laterally (radially outward) from the axis of the catheter towards the target tissue. Once the target tissue is reached the EP ablates. When complete the EP moves the point ablator a small distance to overlap the prior ablation point. Notably, the anchored catheter 103 acts as a platform from which the point ablator can be maneuvered.

With a point ablator a procedural option is to perform all the PVI ablations, and thereby the anchor is inserted into and removed from each PV, after each PV is isolated. After PVI is complete for all the PVs, the umbrella ablator is removed, then the point ablator is inserted. The process of inserting and removing the anchor into each PV is repeated for the point ablator and subsequent creation of the neighboring linear lesions of each PV. A second procedural option is to remove the umbrella ablator after each PV is isolated, then insert the point ablator and perform the linear lesion ablation while the anchor remains seated in the PV, after which the anchor is removed and then inserted into the next PV.

In addition, to insure that the catheter is as secure of a platform as appropriate from which to push the single electrode, or point ablator catheter against the atrial wall, in order to optimize contact, it is desirable to maintain the anchor and umbrella ablator in the pulmonary vein. With those components in place the EP pulls the catheter proximally as tight as possible without disruption to the pulmonary vein in order to keep the catheter sufficiently tight. In case this if insufficient, a restraint is needed to stop the catheter from sagging inside the left atrium.

Reference is made to FIG. 17 showing an exemplary restraint as a balloon support 1710. In other embodiments, the restraint can be constructed as a group of struts that open similar to restrict distal motion with respect to the septal wall. The balloon support 1710 or other restraint structure assists in preventing the catheter 103 from sagging while performing ablations and before and/or after the ablations are performed.

R. System for Performing Cardiac Ablation

Figure 18:
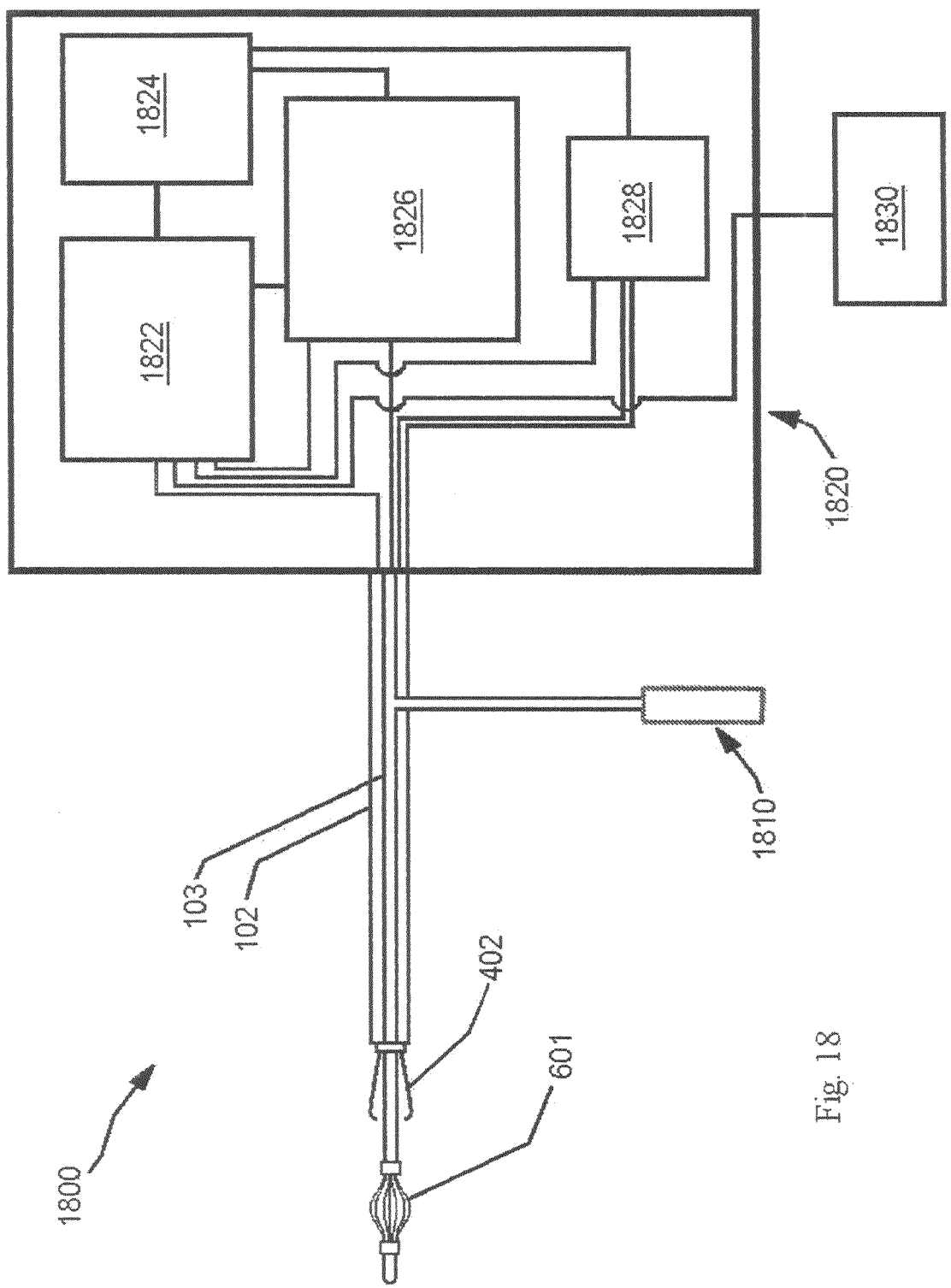
FIG. 18 is a schematic diagram of a system employing an anchoring cardiac ablation device in accordance with the illustrative embodiments.

Reference is now made to FIG. 18 showing an overview of system 1800 employing an anchoring device 601 and an ablator device 402 for performing cardiac ablations in accordance with any of the implementations herein. As shown, a mushroom anchor 601 is employed and an umbrella ablator 402 is employed, however any anchoring and ablating devices can be employed in accordance with the teachings herein. A controller 1810 is operatively connected to the catheter 103 to control the ablator 402 and the anchor 601. The anchor 601, ablator 402 and controller 1810 are also operatively connected to a system server 1820 that controls functionality of the overall system 1800. The system server 1820 can be a stand-alone computer (or other processor), a computing application, a set of software instructions configured to carry out the functions within the system 1800, or other combinations or software and hardware components in accordance with the teachings herein. The system server 1820 includes an application 1822 that includes all functions and applications of the system. This includes instructions for performing the various tasks and other functionalities of performing the anchoring and ablation as described herein. The system server 1820 also includes a power supply 1824 for the components thereof. This power supply can be within the system server 1820 as shown, or as a separate component in other embodiments. A Radio Frequency (RF) generator 1826 is also provided to generate the appropriate signals for performing various functions in the diagnostic or therapeutic procedures described herein, including cardiac ablation. Other energy modes and accompanying generators can also be used instead of RF. There is also included an irrigation pump 1828 as conventionally provided during these diagnostic and/or therapeutic procedures. A display 1830 can also be provided, which is operatively connected to the system server 1820 for displaying appropriate data and information as desired.

It should now be apparent that the various anchoring and ablating catheters described herein are generally applicable in performing cardiac ablations and similar related procedures. Any of the anchoring devices can be combined with any ablator devices as described herein without departing from the scope and purpose of the teachings herein.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, various combinations of anchoring devices and/or ablator devices have been shown and are described together. Any combination of anchor and ablator devices can be employed in accordance with the teachings herein. In addition, directional and locational terms such as "top", "bottom", "front", "back", and "side" should be taken as relative conventions only, and are not absolute. By way of example, in further embodiments, the deployment of the umbrella anchor or balloon anchor can utilize a novel catheter that is dedicated to the placement of the anchor in a manner similar to techniques in which practitioners place a conventional stent. In such embodiment, subsequent t placement of the anchor, the practitioner is free to insert a commercially available ablator of any appropriate configuration. Illustratively, a replacement coupling mechanism can be operatively connected to the distal tip of the conventional ablation catheter. This mechanism and features on the anchor can allow the distal tip of the conventional ablator to be guided into a latching mechanism. When the illustrative ablations are complete, then the resulting latched catheter can withdraw the anchor for removal. Accordingly, this description is meant to be taken only by way of example, and not to otherwise limit the scope of this invention.

What is claimed is:

1. An ablation device, the ablation device comprising:
a body comprising a distal tip;
a sheath slidable over the body;
an ablation apparatus directly coupled to the body and proximal the distal tip, wherein the ablation apparatus comprises a retracted configuration and a deployed configuration that comprises radial expansion of the ablation apparatus in a manner that provides a circumferential arrangement of the ablation apparatus relative to the body, wherein the ablation apparatus further comprises multiple independent segments, each of the multiple independent segments comprises at least one electrode and each of the multiple independent segments being individually reactive to the contours of a target tissue; and
an anchor directly coupled to the body, wherein the anchor comprises a retracted configuration, a fully deployed configuration, and a plurality of actively controlled deployed positions between the retracted configuration and the fully deployed configuration that comprise radial expansion of the anchor in a manner that centers the body with respect to a lumen in which the ablation device is deployed, wherein the anchor comprises one or more sensors for measuring engagement between the anchor and the lumen wall and a resulting force upon the lumen wall in response to radial expansion of the anchor within the lumen and providing the measurement data to an external control system including a controller to which the ablation device is configured to be operatively coupled, the external control system comprising a set of software instructions associated with operation of the anchor and a processor programmed, based on the set of software instructions, to receive the measurement data, determine a force upon the lumen wall based on the measurement data, and provide feedback indicative of a predetermined force measurement level sufficient for maintaining positioning of the anchor within the lumen, wherein the anchor is positively actuatable, via a user-operated active control mechanism of the controller, from the retracted configuration to one of the plurality of deployed positions determined to be sufficient for maintaining positioning of the anchor within the lumen based, at least in part, on the feedback provided from the control system, wherein the anchor does not include any ablation electrodes, and wherein the anchor and ablation apparatus are coaxially aligned with one another along the body,
wherein transition of the ablation apparatus between the retracted and deployed configurations and movement along the body is separate and independent from transition of the anchor between the retracted and one of the plurality of actively controlled deployed positions,
wherein the ablation device is configured such that retraction of the sheath exposes both the anchor and the ablation apparatus.

2. The ablation device according to claim 1, wherein each of the multiple independent segments is a strut and each strut comprises a first portion and a second portion, the second portion being oriented at an angle to the first portion.

3. The ablation device according to claim 2, wherein the at least one electrode is located along the second portion.

4. The ablation device according to claim 3, wherein the ablation apparatus further comprises at least one contact sensor operably coupled to the ablation apparatus, that provides feedback to an operator that the ablation apparatus is in contact with a target tissue.

5. The ablation device according to claim 2, wherein the ablation apparatus comprises a sensor associated with each of the at least one electrode, the sensor being located on the second portion of the strut.

6. A method for ablating a target tissue, the method comprising:
providing an ablation device comprising:
a body comprising a distal tip;
a sheath slidable over the body;
an ablation apparatus directly coupled to the body and proximal the distal tip, wherein the ablation apparatus comprises a retracted configuration and a deployed configuration that comprises radial expansion of the ablation apparatus in a manner that provides a circumferential arrangement of the ablation apparatus relative to the body, wherein the ablation apparatus further comprises multiple independent segments, each of the multiple independent segments comprises at least one electrode and each of the multiple independent segments being individually reactive to the contours of a target tissue; and
an anchor directly coupled to the body, wherein the anchor comprises a retracted configuration, a fully deployed configuration, and a plurality of actively controlled deployed positions between the retracted configuration and the fully deployed configuration that comprise radial expansion of the anchor in a manner that centers the body with respect to a lumen in which the ablation device is deployed, wherein the anchor comprises one or more sensors for measuring engagement between the anchor and the lumen wall and a resulting force upon the lumen wall in response to radial expansion of the anchor within the lumen and providing the measurement data to an external control system including a controller to which the ablation device is configured to be operatively coupled, the external control system comprising a set of software instructions associated with operation of the anchor and a processor programmed, based on the set of software instructions, to receive the measurement data, determine a force upon the lumen wall based on the measurement data, and provide feedback indicative of a predetermined force measurement level sufficient for maintaining positioning of the anchor within the lumen, wherein the anchor is positively actuatable, via a user-operated active control mechanism of the controller, from the retracted configuration to one of the plurality of deployed positions determined to be sufficient for maintaining positioning of the anchor within the lumen based, at least in part, on the feedback provided from the control system, wherein the anchor does not include any ablation electrodes, and wherein the anchor and ablation apparatus are coaxially aligned with one another along the body, wherein transition of the ablation apparatus between the retracted and deployed configurations and movement along the body is separate and independent from transition of the anchor between the retracted and one of the plurality of actively controlled deployed positions, wherein the ablation device is configured such that retraction of the sheath exposes both the anchor and the ablation apparatus;

inserting the ablation device into a lumen of a vessel;

deploying the anchor from the retracted configuration to one of the plurality of actively controlled deployed positions;

deploying the ablation apparatus from the retracted configuration to the deployed configuration; and ablating a surface of the target tissue.

7. The method according to claim 6, wherein the vessel is a pulmonary vein and the target tissue is an atrial wall.

8. The method according to claim 6, wherein each independent segment is a strut and each strut comprises a first portion and a second portion, the second portion being oriented at an angle to the first portion.

9. The method according to claim 8, wherein the electrode is located along the second portion.

10. The method according to claim 9, wherein the ablation apparatus further comprises at least one sensor operably coupled to the ablation apparatus that provides feedback to an operator that the ablation apparatus is in contact with a target tissue.

11. The method according to claim 10, wherein the ablation apparatus comprises a sensor associated with each electrode, each sensor being located on the second portion.

12. The method according to claim 6, wherein the anchor is selected from the group consisting of a balloon anchor, a stent anchor, a mushroom anchor and a mushroom balloon anchor.

* * * * *